United States Patent
Madsen et al.

(10) Patent No.: US 11,752,294 B2
(45) Date of Patent: Sep. 12, 2023

(54) RESPIRATORY ACCESS ASSEMBLY WITH IMPROVED SEAL ASSEMBLY

(71) Applicant: Avent, Inc., Alpharetta, GA (US)

(72) Inventors: Edward B. Madsen, Cumming, GA (US); Angela G. Mitchell, Atlanta, GA (US)

(73) Assignee: Avent, Inc., Alpharetta, GA (US)

( * ) Notice: Subject to any disclaimer, the term of this patent is extended or adjusted under 35 U.S.C. 154(b) by 931 days.

(21) Appl. No.: 16/263,375

(22) Filed: Jan. 31, 2019

(65) Prior Publication Data

US 2020/0246578 A1   Aug. 6, 2020

(51) Int. Cl.
| | |
|---|---|
| A61M 16/20 | (2006.01) |
| A61M 16/00 | (2006.01) |
| A61M 16/04 | (2006.01) |
| A61M 16/08 | (2006.01) |
| A61M 39/06 | (2006.01) |

(52) U.S. Cl.
CPC ...... A61M 16/201 (2014.02); A61M 16/0003 (2014.02); A61M 16/0409 (2014.02); A61M 16/0816 (2013.01); A61M 39/0613 (2013.01); A61M 16/0463 (2013.01); A61M 16/0486 (2014.02)

(58) Field of Classification Search
CPC ............ A61M 16/201; A61M 16/0003; A61M 16/0409; A61M 16/0816; A61M 39/0613; A61M 16/0486; A61M 16/0463
See application file for complete search history.

(56) References Cited

U.S. PATENT DOCUMENTS

| | | | |
|---|---|---|---|
| 3,319,843 A | 5/1967 | Stull | |
| 5,501,377 A | 3/1996 | Dubach | |
| 5,715,815 A | 2/1998 | Lorenzen et al. | |
| | (Continued) | | |

FOREIGN PATENT DOCUMENTS

| | | |
|---|---|---|
| DE | 102014216971 A1 | 3/2016 |
| FR | 2772280 A1 | 6/1999 |
| | (Continued) | |

OTHER PUBLICATIONS

International Search Report and Written Opinion for PCT/US2020/015139, dated May 14, 2020, 11 pages.

*Primary Examiner* — Kendra D Carter
*Assistant Examiner* — Arielle Wolff
(74) *Attorney, Agent, or Firm* — Dority & Manning, P.A.

(57) ABSTRACT

A respiratory access assembly may include a manifold having a first mating surface defining a first port opening. The respiratory access assembly may include a rotatable adapter having a second mating surface defining a second port opening and a seal assembly disposed between the manifold and the rotatable adapter that includes a first seal ring, a second seal ring, and an outer seal ring disposed proximate an outer perimeter of at least one of the manifold or the rotatable adapter. The rotatable adapter may be rotatable relative to the manifold between an open configuration and a closed configuration. The seal assembly may include a connection portion connected between the first seal ring and the second seal ring. The connection portion may form a seal between the first mating surface and the second mating surface between the first seal ring and the second seal ring.

15 Claims, 12 Drawing Sheets

(56) References Cited

U.S. PATENT DOCUMENTS

| | | | |
|---|---|---|---|
| 5,735,271 A * | 4/1998 | Lorenzen | A61M 16/0463 |
| | | | 128/200.26 |
| 6,494,203 B1 | 12/2002 | Palmer | |
| 6,612,304 B1 * | 9/2003 | Cise | A61M 16/0463 |
| | | | 128/207.14 |
| 6,615,835 B1 | 9/2003 | Cise et al. | |
| 7,152,603 B1 | 12/2006 | Crump et al. | |
| 7,182,746 B2 | 2/2007 | Haarala et al. | |
| 7,503,902 B2 | 3/2009 | Jensen et al. | |
| 8,414,544 B2 * | 4/2013 | Resca | A61M 3/0279 |
| | | | 604/248 |
| 8,544,463 B2 * | 10/2013 | Brewer | B29C 45/1676 |
| | | | 128/200.24 |
| 2002/0062106 A1 | 5/2002 | Chu et al. | |
| 2009/0143723 A1 | 6/2009 | Szpara et al. | |
| 2010/0147310 A1 * | 6/2010 | Brewer | A61M 16/0463 |
| | | | 128/207.14 |
| 2012/0073575 A1 | 3/2012 | Brewer et al. | |
| 2013/0218071 A1 | 8/2013 | Resca | |
| 2016/0089071 A1 | 3/2016 | Crawford et al. | |
| 2016/0114129 A1 | 4/2016 | Lancette | |
| 2017/0165466 A1 | 6/2017 | Lorimer et al. | |
| 2018/0021561 A1 | 1/2018 | Nelson et al. | |
| 2019/0134338 A1 * | 5/2019 | Mansi | A61M 16/0463 |

FOREIGN PATENT DOCUMENTS

| WO | WO 96/26757 A1 | 9/1996 |
|---|---|---|
| WO | WO 99/34849 A1 | 7/1999 |
| WO | WO 02/28463 A2 | 4/2002 |

\* cited by examiner

RESPIRATORY ACCESS ASSEMBLY WITH IMPROVED SEAL ASSEMBLY

FIELD OF THE INVENTION

The present invention relates generally to the field of respiratory care systems for intubated patients, and more specifically to a respiratory access assembly having an improved seal assembly.

BACKGROUND OF THE INVENTION

Proper long-term respiratory care of intubated patients often requires that multiple, and often simultaneous, medical procedures be performed on the patient. Example procedures can include ventilation of the patient's lungs, aspiration of secretions from the lungs, oxygenation of the lungs, elimination or reduction of residual $CO_2$ from the lungs, visual inspection of portions of the respiratory system, sampling sputum and gases, sensing parameters, such as flow rates, pressure, and temperature of gases within the respiratory system, and/or the administration of medication, gases, and/or lavage.

Patients having low lung capacity, such as premature babies and adults suffering from emphysema, may sometimes require simultaneous procedures. In such patients, it is important to remove secretions which have accumulated in the respiratory system without starving the patient for oxygen during the secretion removal process and without introducing contaminates into the respiratory system.

Medical care providers thus need a respiratory care assembly to efficiently and safely permit multiple procedures to be performed while minimizing stress to the patient by controlling access to the ventilator circuit that minimizes or reduces loss of positive-end expiratory pressure (PEEP).

SUMMARY OF THE INVENTION

Objects and advantages of the invention will be set forth in the following description, or may be obvious from the description, or may be learned through practice of the invention.

In accordance with aspects of the invention, a respiratory access assembly may include a manifold having a first mating surface defining a first port opening. The respiratory access assembly may include a rotatable adapter having a second mating surface defining a second port opening. The respiratory access assembly may include a seal assembly disposed between the manifold and the rotatable adapter. The seal assembly may include a first seal ring, a second seal ring, and an outer seal ring disposed proximate an outer perimeter of at least one of the manifold or the rotatable adapter. The rotatable adapter may be rotatable relative to the manifold between an open configuration and a closed configuration. In the open configuration, the first port opening of the manifold may be aligned with the second port opening and sealed with the second port opening by the first seal ring of the seal assembly to form a fluid connection between the first port opening of the manifold and the second port opening of the rotatable adapter. In the closed configuration, the first port opening of the manifold may be sealed with a portion of the second mating surface of the rotatable adapter by the second seal ring of the seal assembly. The seal assembly may include a connection portion connected between the first seal ring and the second seal ring. The connection portion may form a seal between the first mating surface and the second mating surface between the first seal ring and the second seal ring.

In a particular embodiment, the seal assembly may be countersunk with respect to the first mating surface of the manifold such that an outer sealing surface of the seal assembly is approximately flush with the first mating surface.

In another particular embodiment, the seal assembly may be countersunk with respect to second mating surface of the manifold such that an outer sealing surface of the seal assembly is approximately flush with the second mating surface.

In another particular embodiment, the seal assembly may include at least one spoke connected between the outer seal ring and at least one of the first seal ring or the second seal ring.

In another particular embodiment, the seal assembly may include a continuous surface defined between the outer seal ring and each of the first seal ring and second seal ring.

In another particular embodiment, the outer seal ring of the seal assembly may include a portion of the seal assembly that is proximate a perimeter of the seal assembly. The portion of the seal assembly may be raised relative to the continuous surface in a direction perpendicular to the continuous surface.

In another particular embodiment, at least one of the first seal ring or second seal ring may include a portion of the seal assembly that is raised relative to the continuous surface in a direction perpendicular to the continuous surface.

In another particular embodiment, the seal assembly may be attached to at least one of the manifold or rotatable adapter.

In another particular embodiment, the seal assembly may be over molded onto the first mating surface of the manifold or the second mating surface of the rotatable adapter.

In another particular embodiment, the respiratory access assembly may include a ventilator manifold that is configured to be attached to an artificial airway that extends into a respiratory tract of a patient. At least one of the first port opening or second port opening may be coupled with the ventilator manifold.

In another particular embodiment, the respiratory access assembly may include a catheter assembly that includes a catheter tube. At least one of the first port opening or second port opening may be coupled with the catheter assembly such that the catheter tube is slidable through the first port opening and second port opening when the rotatable adapter is in the open configuration.

In another particular embodiment, one of the manifold or rotatable adapter may include a snap ring feature that is configured to engage a portion of another of the manifold or rotatable adapter to couple the manifold and rotatable adapter together.

In accordance with another aspect of the invention, a method of forming a respiratory access assembly may include forming a manifold having a first mating surface defining a first port opening. The method may include forming a rotatable adapter having a second mating surface defining a second port opening. The method may include arranging a seal assembly between the first mating surface of the manifold and the second mating surface of the rotatable adapter. The seal assembly may include a first seal ring, a second seal ring, and an outer seal ring disposed proximate an outer perimeter of at least one of the manifold or the rotatable adapter. The rotatable adapter may be rotatable relative to the manifold between an open configuration and a closed configuration. In the open configuration, the first port opening of the manifold may be aligned with the second port opening and sealed with the second port opening by the first seal ring in the seal assembly to form a fluid connection between the first port opening of the manifold and the second port opening of the rotatable adapter. In the closed configuration, the first port opening of the manifold may be sealed with a portion of the second mating surface of the rotatable adapter by the second seal ring of the seal assembly. The seal assembly may include a connection portion connected between the first seal ring and the second seal ring. The connection portion may form a seal between the first mating surface and the second mating surface between the first seal ring and the second seal ring.

In a particular embodiment, at least one of forming the manifold or forming the rotatable adapter may include injection molding the at least one of the manifold or the rotatable adapter.

In another particular embodiment, arranging the seal assembly between the first mating surface of the manifold and the second mating surface of the rotatable adapter may include attaching the seal assembly to at least one of the first mating surface of the manifold or the second mating surface of the rotatable adapter.

In another particular embodiment, arranging the seal assembly between the first mating surface of the manifold and the second mating surface of the rotatable adapter may include over molding the seal assembly to at least one of the first mating surface of the manifold or the second mating surface of the rotatable adapter.

In another particular embodiment, the method may include countersinking the seal assembly with respect to the first mating surface of the manifold such that an outer sealing surface of the seal assembly is approximately flush with the first mating surface.

In another particular embodiment, the method may include countersinking the seal assembly with respect to the second mating surface of the rotatable adapter such that an outer sealing surface of the seal assembly is approximately flush with the second mating surface.

In another particular embodiment, the method may include integrally forming a snap ring feature with one of the manifold or the rotatable adapter that is configured to engage a portion of another of the manifold or rotatable adapter to couple the manifold and rotatable adapter together.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Repeat use of reference characters in the present specification and drawings is intended to represent the same or analogous features or elements of the present invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents. For the purposes of this application, like features will be represented by like numbers between the figures.

Generally speaking, the present invention is directed to a respiratory access assembly configured to provide improved sealing. The improved sealing can prevent or reduce the introduction of contaminates into the patient's airway. The improved sealing can provide improved suction and/or delivery of a substance (e.g., water, medicine, etc.), for example to perform lavage.

The respiratory access assembly can be adjustable between an open configuration, in which the ports are aligned and fluidly connected, and a closed configuration, in which the ports are fluidly separated. A catheter assembly can be connected with the first port to perform medical procedures with respect to the patient's airway. The second port can be connected with a device, such as an endotracheal tube, for insertion into the patient's airway.

In the open configuration, a catheter tube may be slidable through the first and second port openings and through the artificial airway (e.g., through the endotracheal tube) that extends into the respiratory tract of the patient to perform one or more medical procedures on the patient. The medical procedure(s) can include suctioning to remove material (e.g., secretions) accumulated in the respiratory system of the patient and/or delivering a substance into the respiratory system of the patient.

In the closed configuration, the first and second ports can be fluidly separated such that the catheter assembly can be detached from the respiratory access assembly. The catheter assembly may be removed or detached to be cleaned, replaced, or the like. Because the first and second ports are fluidly separated, however, the catheter assembly can be detached without opening the ventilator circuit, which can cause a loss of positive-end expiratory pressure (PEEP).

The respiratory access assembly can include a seal assembly that is configured to provide such improved fluid separation between the ports. For example, the seal assembly may include a connection portion extending between the two ports, as described herein.

More specifically, the respiratory access assembly can include a manifold having a first mating surface defining a first port opening and a rotatable adapter having a second mating surface defining a second port opening. The seal assembly can be disposed between the manifold and the rotatable adapter. The seal assembly can include a first seal ring, a second seal ring, and an outer seal ring disposed proximate an outer perimeter of at least one of the manifold or the rotatable adapter.

The rotatable adapter can be rotatable relative to the manifold between the open configuration and the closed configuration. In the open configuration, the first port opening of the manifold can be aligned with the second port opening and sealed with the second port opening by the first seal ring of the seal assembly to form a fluid connection between the first port opening of the manifold and the second port opening of the rotatable adapter. In the closed configuration, the first port opening of the manifold can be sealed with a portion of the second mating surface of the rotatable adapter by the second seal ring of the seal assembly. The seal assembly can include a connection portion connected between the first seal ring and the second seal ring. The connection portion can form a seal between the first mating surface and the second mating surface at a location between the first seal ring and the second seal ring. The connection portion can provide improved fluid separation between the first and second port openings (e.g., when the respiratory access assembly is in the closed configuration).

The components described herein may be formed of a variety of materials and from a variety of manufacturing processes. In some embodiments, the components of the present invention may be injection molded from a medical grade synthetic resinous material such as acrylic, a flexible polyvinylchloride, modified polypropylene, or similar materials.

The seal assembly may be formed of a variety of materials, such as, for example, a silicon rubber, a thermoplastic elastomer, or other similar polymer. In some embodiments, the seal assembly may be bonded in place by heat, adhesive, or sonic welds. In other embodiments, however, the seal assembly may be free of bonding or adhesives. For example, the seal assembly may be frictionally held in place or press-fitted in place.

The seal assembly may be formed using a variety of suitable processes. For example, the seal assembly may be over molded onto one or more of the components. However, it is also to be understood that the seal assembly may be separately formed (e.g., using molding).

Figure 1A:
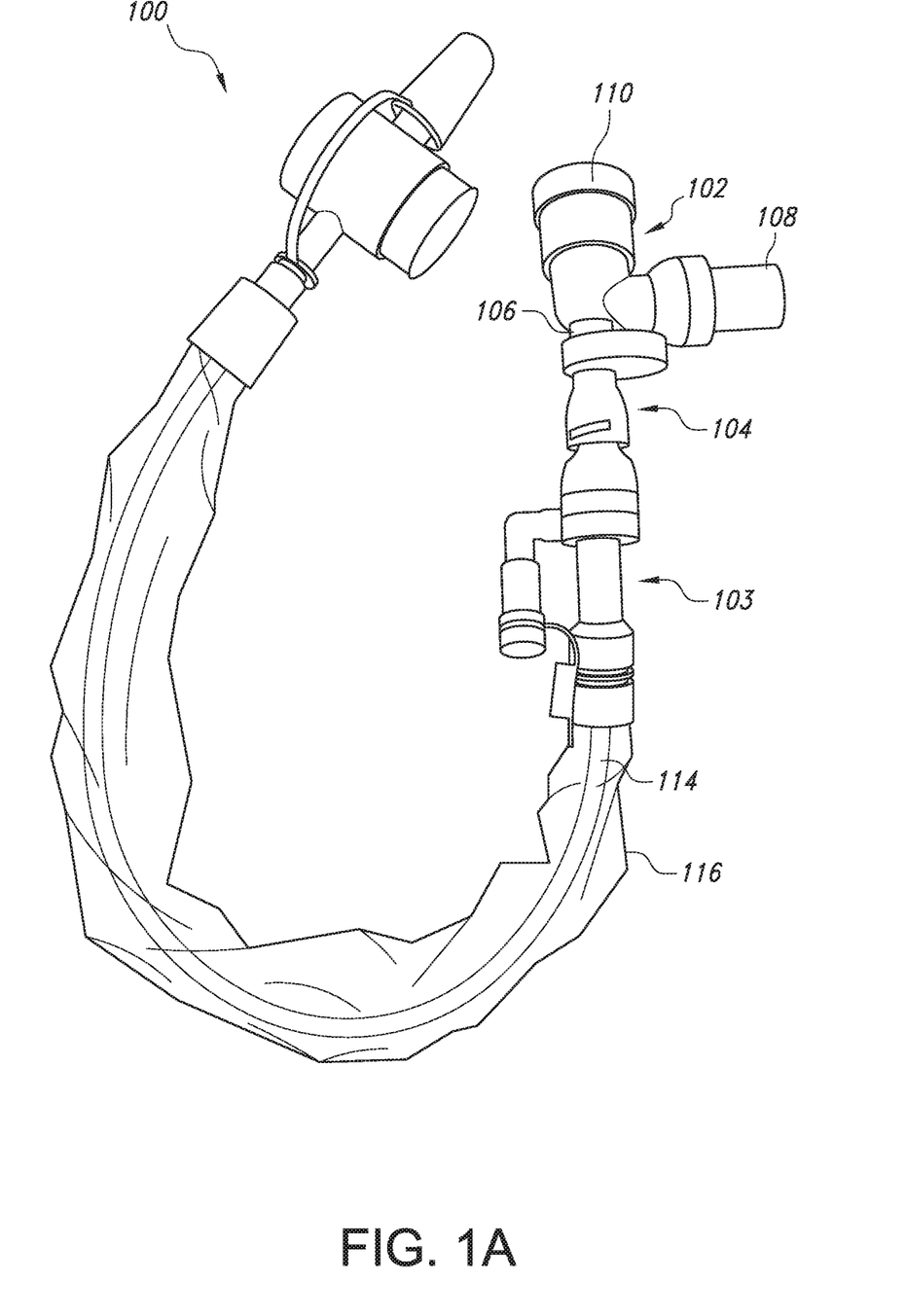
FIG. 1A depicts a respiratory access assembly including a ventilator manifold, a catheter assembly, and a rotatable assembly according to aspects of the present disclosure.
Figure 1B:
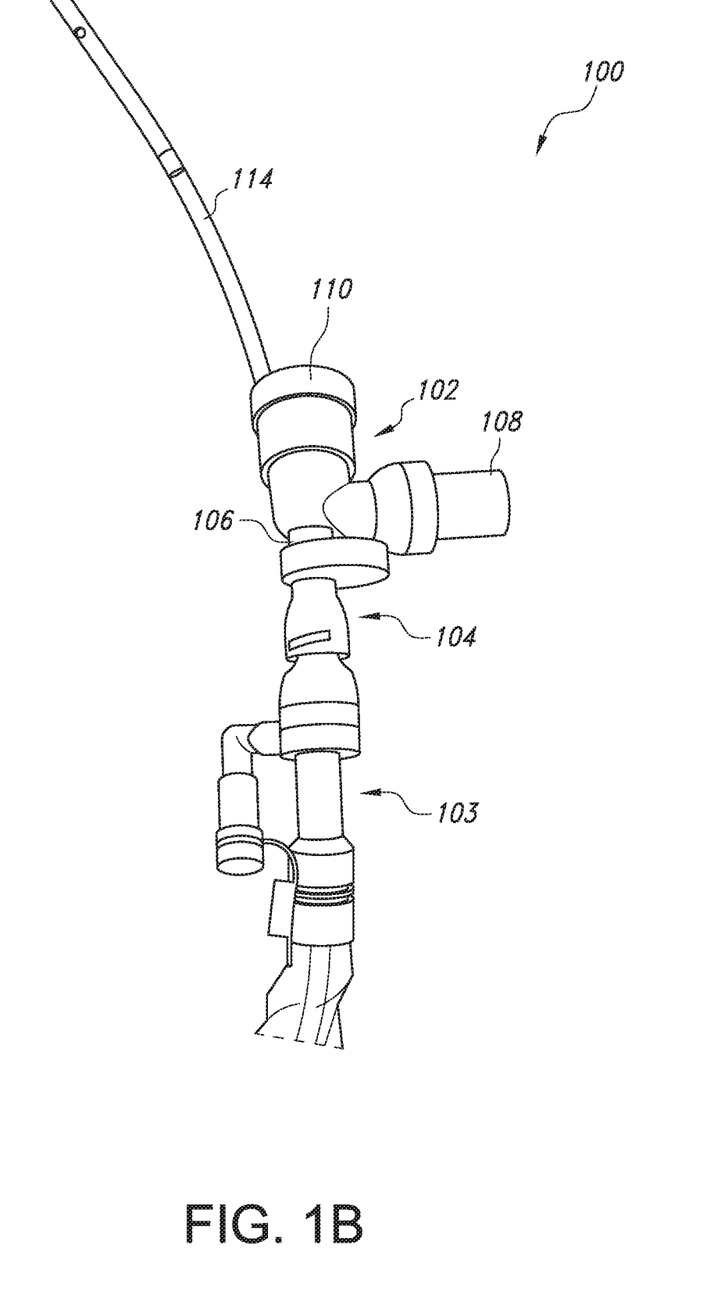
FIG. 1B depicts the respiratory access assembly of FIG. 1A, in which a catheter tube of the catheter assembly extends through the rotatable assembly, which is in the open configuration according to aspects of the present disclosure.

FIGS. 1A and 1B depict a respiratory access assembly 100 according to aspects of the present disclosure. The respiratory access assembly 100 may include a ventilator manifold 102, a catheter assembly 103, and a rotatable assembly 104. The rotatable assembly 104 may be rotatable between an open configuration, for example as described below with reference to FIGS. 1A and 1B, and a closed configured, for example as described below with reference to FIG. 2B. The rotatable assembly 104 may couple with the ventilator manifold 102 at a first port 106 of the ventilator manifold 102. The ventilator manifold 102 may include a ventilator port 108 configured for connecting the assembly 100 to a ventilator system or assisted breathing device. The ventilator manifold 102 may include a second port 110 configured for connecting the respiratory access assembly 100 to a device for insertion into a patient's artificial airway, such as an endotracheal tube. The catheter assembly 112 may include a catheter tube 114 and a sleeve or sheath 116 around the catheter tube 114.

Referring to FIG. 1B, the catheter tube 114 may be slidable through the rotatable assembly 104, when the rotatable assembly 104 is in the open configuration. The catheter tube 114 may slide through the rotatable assembly 104 and into the patient's artificial airway, for example to perform a medical procedure (e.g., suctioning to remove fluid or mucosal secretions from the patient's lungs).

Figure 2A:
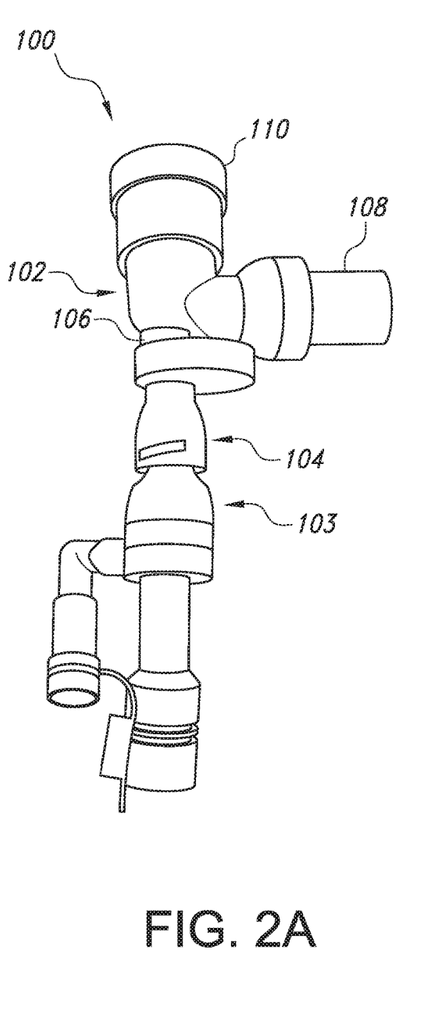
FIGS. 2A and 2B are enlarged views of the respiratory access assembly of FIGS. 1A and 1B in which the rotatable assembly is in the open configuration and closed configurations, respectively.
Figure 2B:
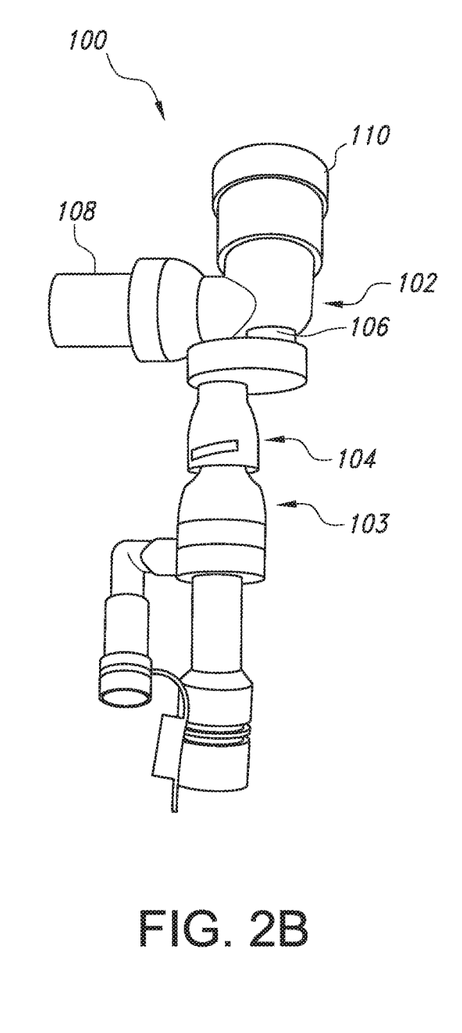

FIGS. 2A and 2B depict the respiratory access assembly 100 of FIGS. 1A and 1B in which the rotatable assembly is in the open and closed configurations, respectively.

Figure 3A:
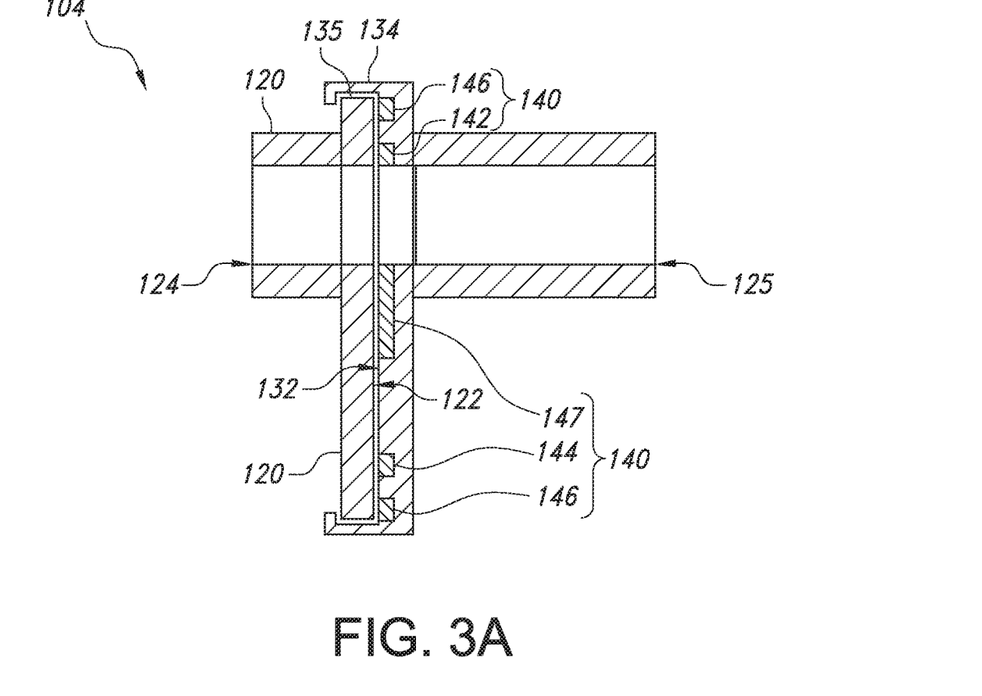
FIGS. 3A and 3B are cross-sectional side views of the rotatable assembly of the respiratory access assembly of FIGS. 1A through 2B in the open configuration and closed configuration, respectively.
Figure 3B:
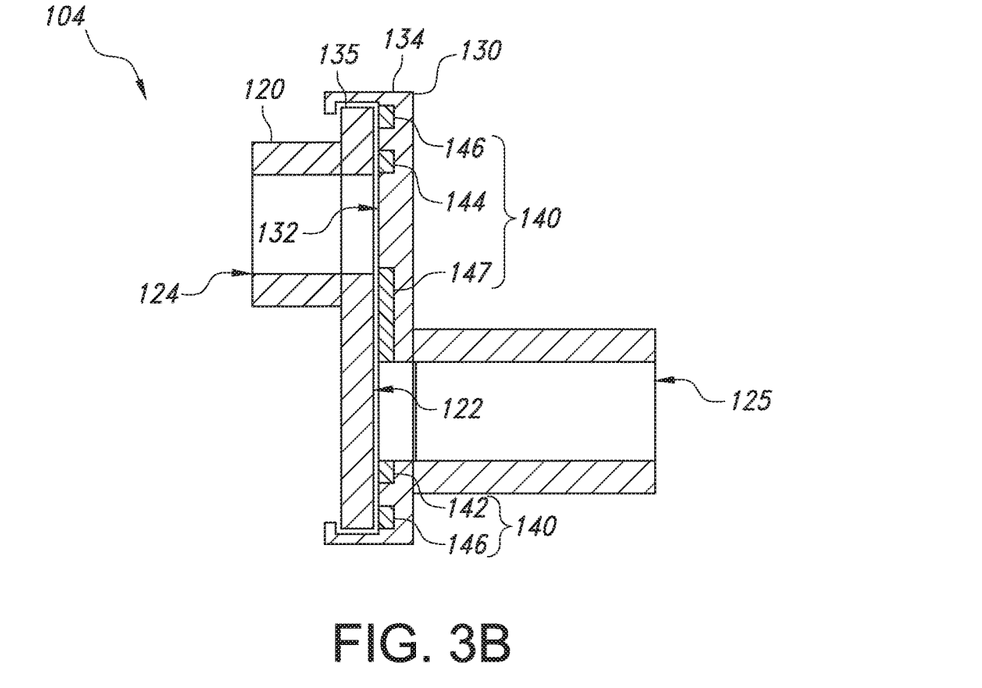

FIGS. 3A and 3B are cross sectional side views of the rotatable assembly 104 of the respiratory access assembly 100 of FIGS. 1A through 2B in the open configuration and closed configuration, respectively. The rotatable assembly 104 may include a manifold 120 having a first mating surface 122. The first mating surface 122 may define a first port opening 124. The rotatable assembly 104 may include a rotatable adapter 130. The rotatable adapter 130 may have a second mating surface 132, which may define a second port opening 125.

The rotatable adapter 130 may be rotatable relative to the manifold 120 between the open configuration, for example as illustrated in FIG. 3A, and the closed configuration, for example as illustrated in FIG. 3B. In the open configuration, (FIG. 3A), the first port opening 124 of the manifold 120 can be aligned with and fluidly coupled with the second port opening 125 of the rotatable adapter 130.

In the closed configuration, (FIG. 3B) the first port opening 124 of the manifold 120 can fluidly sealed from the second port opening 125. More specifically, the first port opening 124 can be fluidly sealed by a seal assembly 140 and a portion of the second mating surface 132.

In some embodiments, the manifold 120 and rotatable adapter 130 may snap together to form the rotatable assembly 104. For example, the rotatable adapter 130 may include a snap ring feature 134 that is configured to engage a portion 135 the manifold 120 to couple the manifold 120 and rotatable adapter 130 together. The portion 135 of the manifold 120 may include an outer circumferential surface of the manifold 120. In other embodiments, however, the manifold 120 may include the snap ring feature and may engage the rotatable adapter 130.

In some embodiments, the rotatable assembly 104 may employ one or more features that provide an indication (e.g., to the clinician) when the rotatable assembly 104 is successfully rotated into the open configuration and/or closed configuration. For example, the rotatable adapter 130 and/or manifold 120 may be configured to produce increased resistance to rotation (e.g., from a "stop" feature), a tactile/audible click, or the like, when the rotatable adapter 130 has been rotated to the desired position.

Figure 4A:
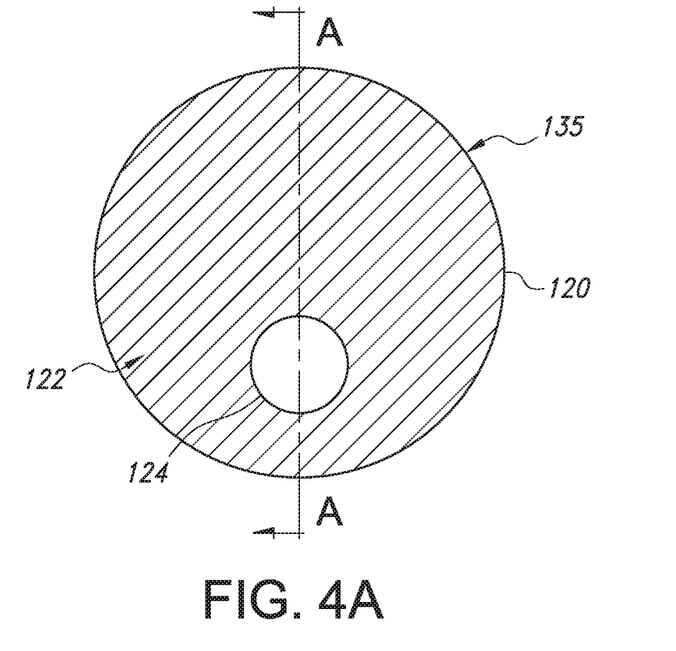
FIG. 4A depicts the manifold of the rotatable assembly of the respiratory access assembly of FIGS. 1A through 2B.
Figure 4B:
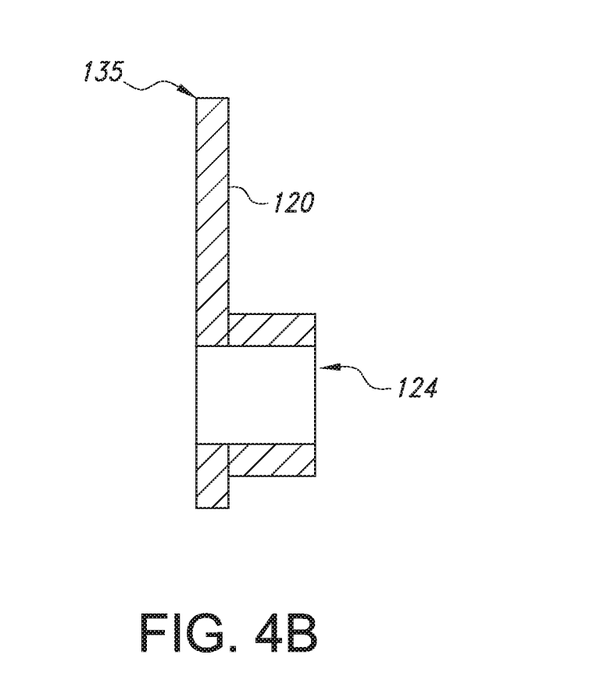
FIG. 4B is a section view along section A-A of FIG. 4A.

FIGS. 4A and 4B depict the manifold 120 of the respiratory access assembly 100 of FIGS. 2A and 2B. FIG. 4B illustrates a cross-sectional view along section A-A of FIG. 4A. As shown, the manifold 120 may include the first port opening 124.

Figure 5A:
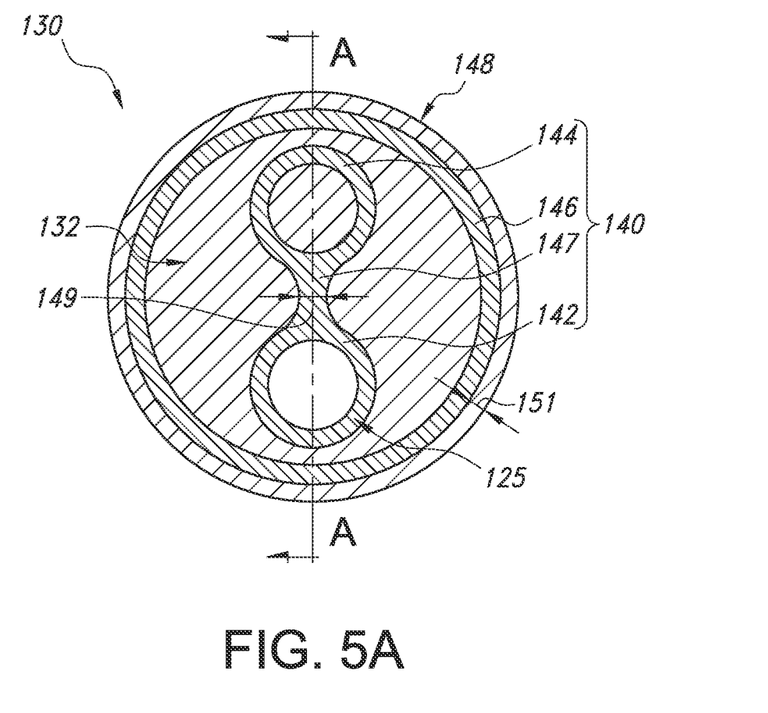
FIG. 5A is a front view of the rotatable adapter of the rotatable assembly of the respiratory access assembly of FIGS. 1A through 3B.
Figure 5B:
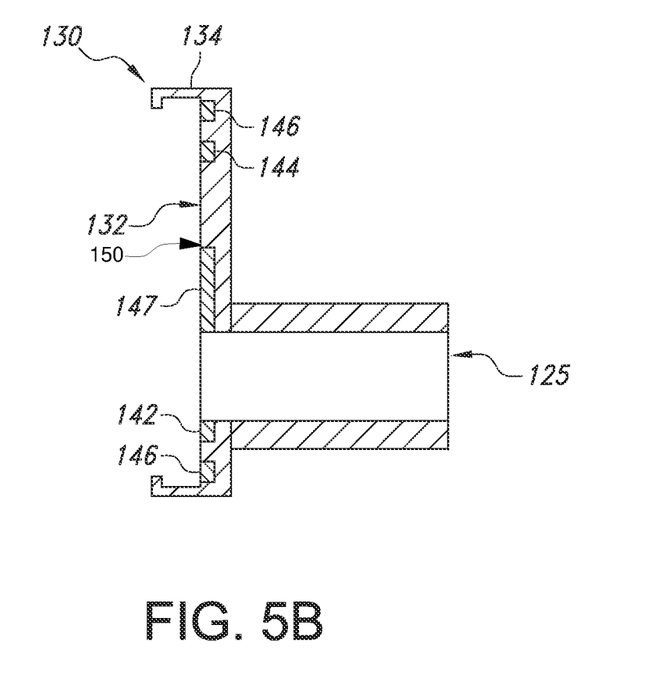
FIG. 5B is a section view of the rotatable adapter of FIG. 5A along section A-A of FIG. 5A.

FIGS. 5A and 5B depict a front view and section view the rotatable adapter 130 of the rotatable assembly 104 of FIGS. 3A and 3B. More specifically, FIG. 5B depicts a cross-sectional view of the rotatable adapter 130 of FIG. 5A along section A-A of FIG. 5A. A seal assembly 140 may be disposed between the manifold 120 and the rotatable adapter 130. The seal assembly 140 may include a first seal ring 142, a second seal ring 144, and a connection portion 147 connected between the first seal ring 142 and the second seal ring 144.

The first seal ring 142 may form a seal between the first port opening 124 of the manifold 120 (FIGS. 3A and 3B) and the second port opening 125 of the rotatable adapter 130 when the rotatable adapter 104 is in the open configuration. In the closed configuration, the second seal ring 144 may form a seal between the first port opening 124 (FIGS. 3A and 3B) and the second mating surface 132 to seal the first port opening 124 against leakage of PEEP.

The connection portion 147 may form a seal between the first mating surface 122 and the second mating surface 132 at a location between the first seal ring 142 and the second seal ring 144. The connection portion 147 may improve fluid separation or isolation between the first port opening 124 and the second port opening 125 when the rotatable assembly 104 is in the closed configuration.

The connection portion 147 may have a variety of suitable shapes and sizes. For example, the connection portion 147 may have a width 149 in a plane parallel with the second mating surface 132. For instance, the width 149 may be defined in a first direction that is perpendicular to a second direction that extends between centers of the first and second seal rings 142, 144. In some embodiments, the width 149 of the connection portion 147 may be less than a diameter of the first port opening 124 (FIG. 4A), a diameter of the second portion opening 125, or both. In other embodiments, however, the width 149 of the connection portion 147 may be greater than a diameter of the first port opening 124 (FIG. 4A), a diameter of the second portion opening 125, or both.

The seal assembly 140 may also include an outer seal ring 146. The outer seal ring 146 may be disposed proximate an outer perimeter 148 of the rotatable adapter 130. For example, the outer seal ring 146 may be inwardly offset with respect to the outer perimeter 148 by an offset distance 151 (e.g., uniformly offset around the outer perimeter 148). In some embodiments, the offset distance 151 may be about zero such that the outer seal ring 146 is approximately aligned with the outer perimeter 148.

Referring to FIG. 5B, the seal assembly 140 (e.g., the first seal ring 142, second seal ring 144, and/or connection portion 147) may be countersunk with respect to the second mating surface 132 of the manifold 120 such that an outer sealing surface is formed by the second mating surface 132 and the seal assembly 140. For example, the seal assembly 140 may be approximately flush with the second mating surface 132 such that the outer sealing surface is generally planar, for example as shown in FIG. 5B.

In other embodiments, however, the seal assembly 140 may be countersunk and/or generally flush with respect to the first mating surface 122 of the manifold 120 such that an outer sealing surface 150 of the seal assembly 140 is approximately flush with the first mating surface 122.

In some embodiments, the seal assembly 140 may be attached to the rotatable adapter 130. However, in other embodiments, the seal assembly 140 may be attached to the manifold 120. For example, the seal assembly 140 may be over molded onto the first mating surface 122 of the manifold 120 or the second mating surface 132 of the rotatable adapter 130.

Figure 6A:
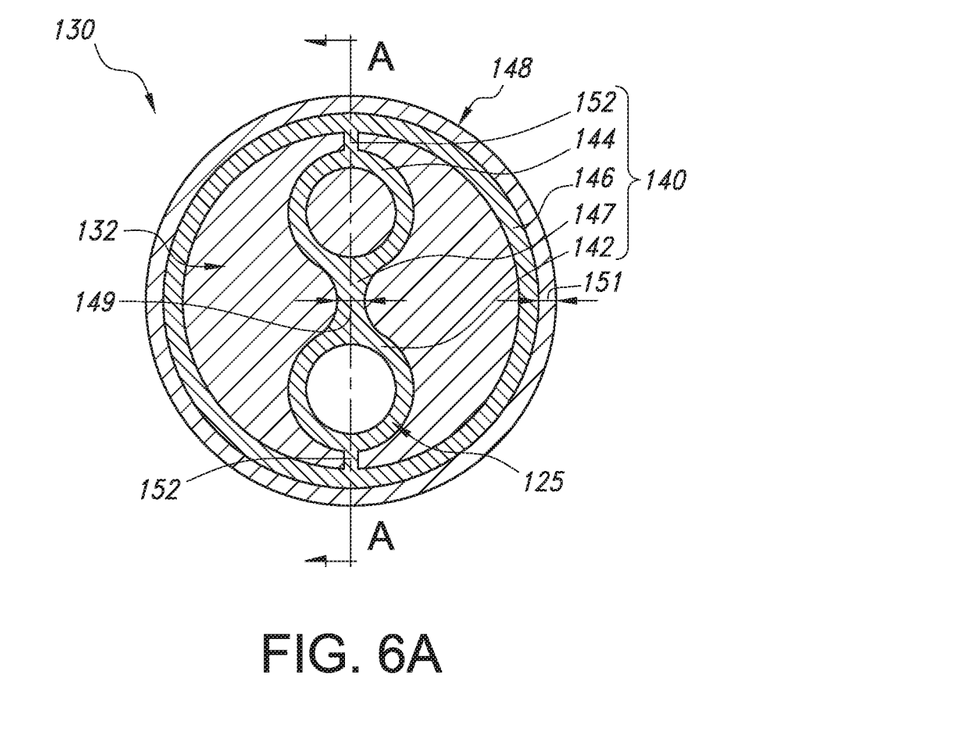
FIG. 6A depicts another embodiment of a rotatable adapter of the rotatable assembly of FIGS. 3A and 3B in which a seal assembly includes at least one spoke connected between an outer seal ring and at least one of a first seal ring or a second seal ring according to aspects of the present disclosure.
Figure 6B:
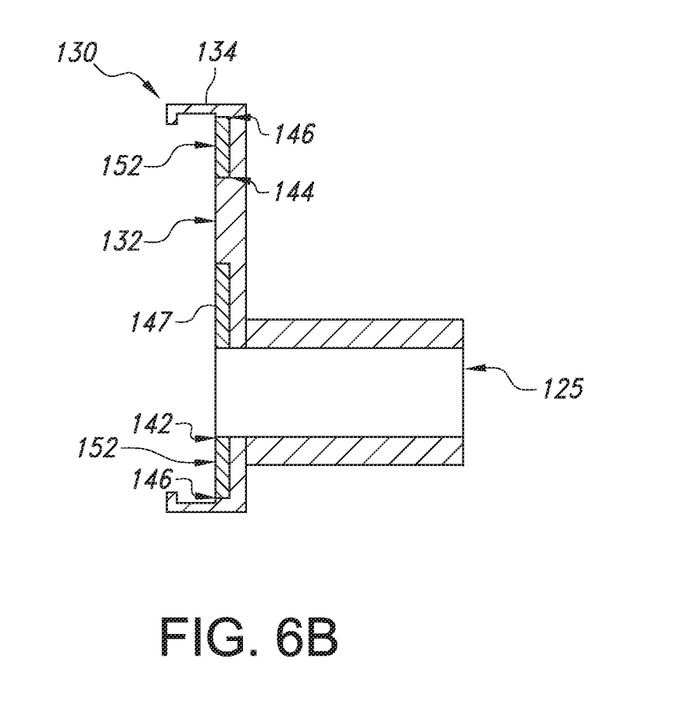
FIG. 6B is a section view of the rotatable adapter of FIG. 6A along section A-A of FIG. 6A.

Referring to FIGS. 6A and 6B, in some embodiments, the seal assembly 140 may include at least one spoke 152 connected between the outer seal ring 146 and at least one of the first seal ring 142 or the second seal ring 144. For example, a pair of spokes 152 may connect the first seal ring 152 and second seal ring 144, respectively, with the outer seal ring 146.

The spoke(s) 152 may provide a variety of benefits. For example, the spoke(s) 152 may prohibit or reduce relative movement between the seal rings 142, 144 and the outer seal ring 146. In such embodiments, the seal assembly 140 may be a single body or piece, which may reduce manufacturing and/or assembly costs associated with the seal assembly 140.

Figure 7A:
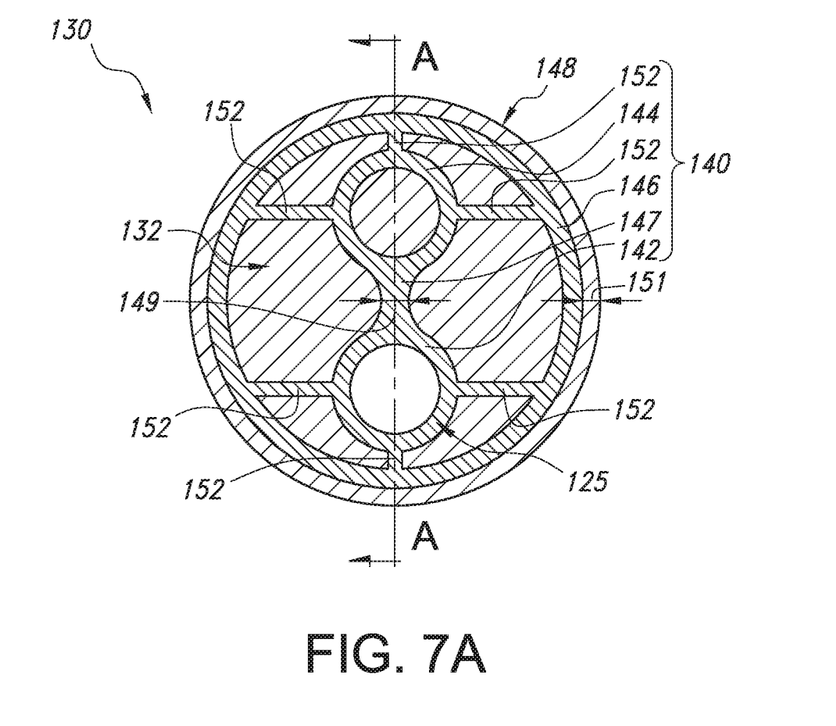
FIG. 7A depicts another embodiment of a rotatable adapter of the rotatable assembly of FIGS. 3A and 3B in which a seal assembly includes multiple spokes connected between an outer seal ring and at least one of a first seal ring or a second seal ring according to aspects of the present disclosure.
Figure 7B:
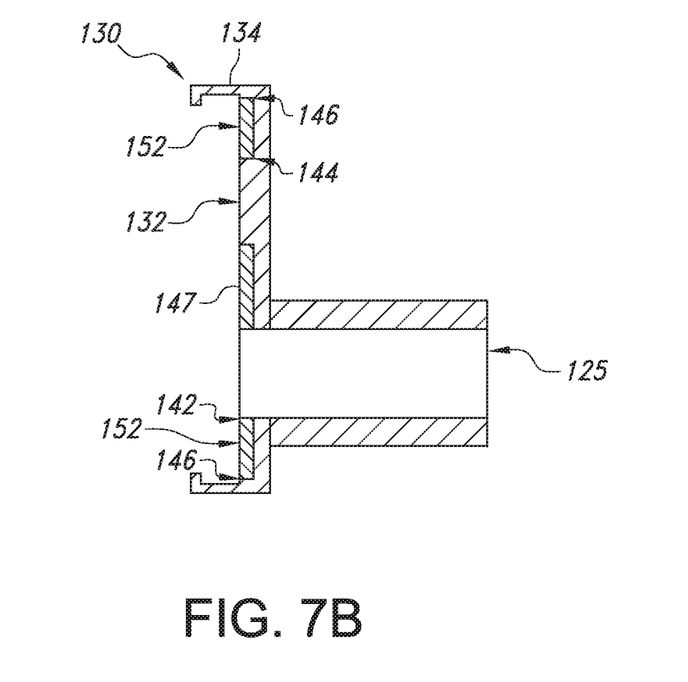
FIG. 7B is a section view of the rotatable adapter of FIG. 7A along section A-A of FIG. 7A.

Referring to FIGS. 7A and 7B, in some embodiments, the seal assembly 140 may include multiple spokes 152 connected between the outer seal ring 146 and the first seal ring 142 and the second seal ring 144. The additional spokes 152 of the seal assembly 140 of FIGS. 7A and 7B as compared with FIGS. 6A and 6B may provide easier manufacturing and/or assembly. Further, the additional spokes 152 may further reduce relative movement between the seal rings 142, 144 and the outer seal ring 146.

Figure 8A:
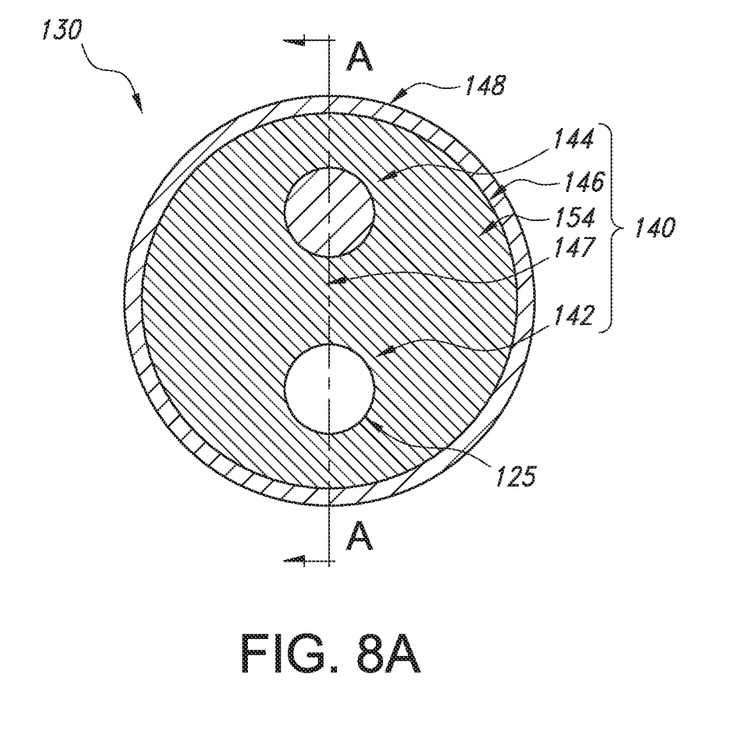
FIG. 8A depicts another embodiment of a rotatable adapter of the rotatable assembly of FIGS. 3A and 3B in which the seal assembly includes a continuous surface defined between the outer seal ring and each of the first seal ring and second seal ring according to aspects of the present disclosure.
Figure 8B:
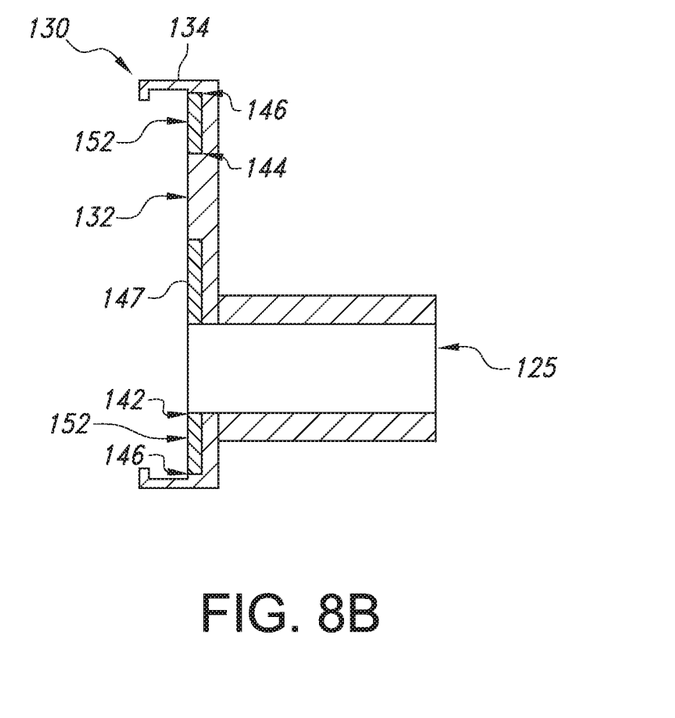
FIG. 8B is a section view of the rotatable adapter of FIG. 8A along section A-A of FIG. 8A.

Referring to FIGS. 8A and 8B, in some embodiments, the seal assembly 140 may include a continuous surface 154 defined between the outer seal ring 146 and each of the first seal ring 142 and second seal ring 144. The continuous surface 154 may provide easier manufacturing and/or assembly of the seal assembly 140. Further, the continuous surface 154 may provide improved sealing, for example between the first seal ring 142 and second seal ring 146 (e.g., corresponding portions of the seal assembly 140). For example, as the rotatable adapter 130 is rotated relative to the manifold 120, the first port opening 124 of the manifold 120 and/or second port opening 125 of the rotatable adapter 130 may maintain contact with the seal assembly 140. As a result, the port openings 124, 125 may remain sealed against the seal assembly 140 during rotation of the rotatable adapter 130 between the open and closed configurations.

Figure 9A:
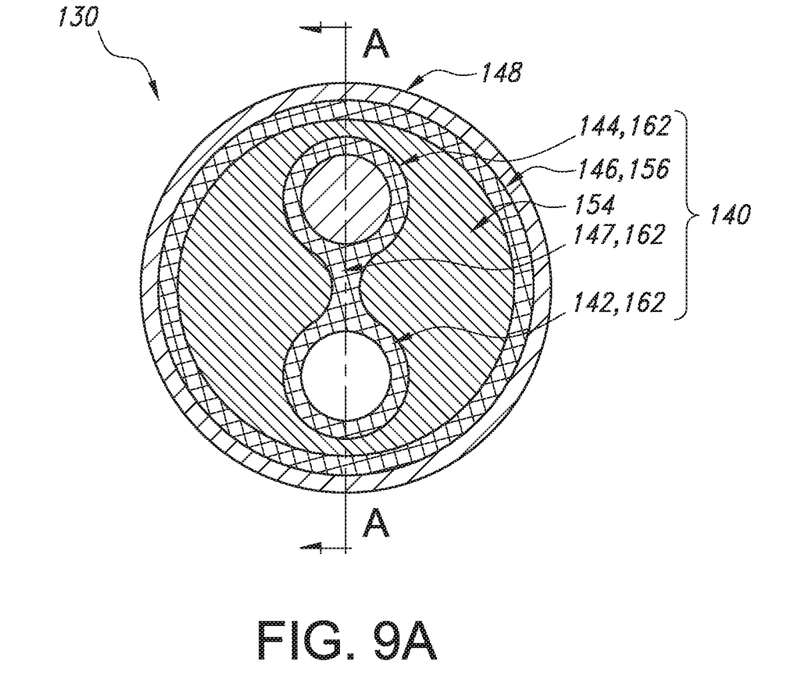
FIG. 9A depicts another embodiment of a rotatable adapter of the rotatable assembly of FIGS. 3A and 3B in which the seal assembly includes a continuous surface and raised portions according to aspects of the present disclosure.
Figure 9B:
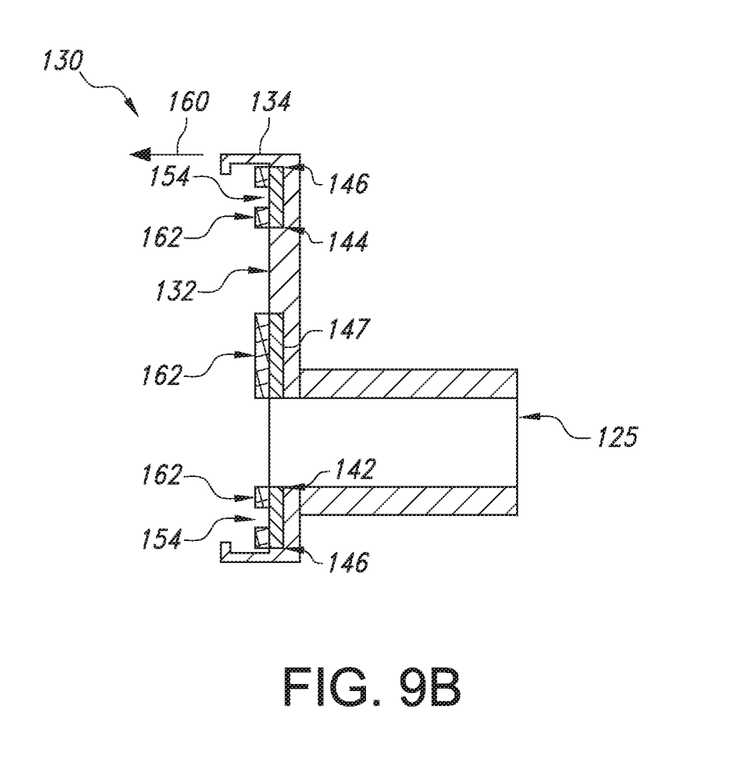
FIG. 9B is a section view of the rotatable adapter of FIG. 9A along section A-A of FIG. 9A.

Referring to FIGS. 9A and 9B, in some embodiments, the seal assembly 140 may include a first raised portion 156 of the seal assembly 140 proximate a perimeter 158 of the seal assembly 140 that is raised relative to the continuous surface 154 in a direction 160 perpendicular to the continuous surface 154. In some embodiments, at least one of the first seal ring 142, second seal ring 144, and/or connection portion 147 may comprise a second raised portion 162 that is raised relative to the continuous surface 154 in the direction 160 perpendicular to the continuous surface 154.

The first raised portion 156 may improve sealing between the seal assembly 140 and the manifold 120 along the perimeter 158 of the seal assembly 140, which may prevent contaminates or other foreign matter from entering the rotatable adapter 104. The second raised portion 162 may provide improved sealing in the open and closed configurations while the continuous surface 154 may still provide sealing while the rotatable adapter 130 is being rotated between the open configuration and the closed configuration. For example, the second raised portion 162 may provide improved sealing between the second port opening 125 and the first port opening 124 in the open configuration. The second raised portion 162 may tightly seal the first port opening 124 against the continuous surface 154 in the closed configuration.

Figure 10A:
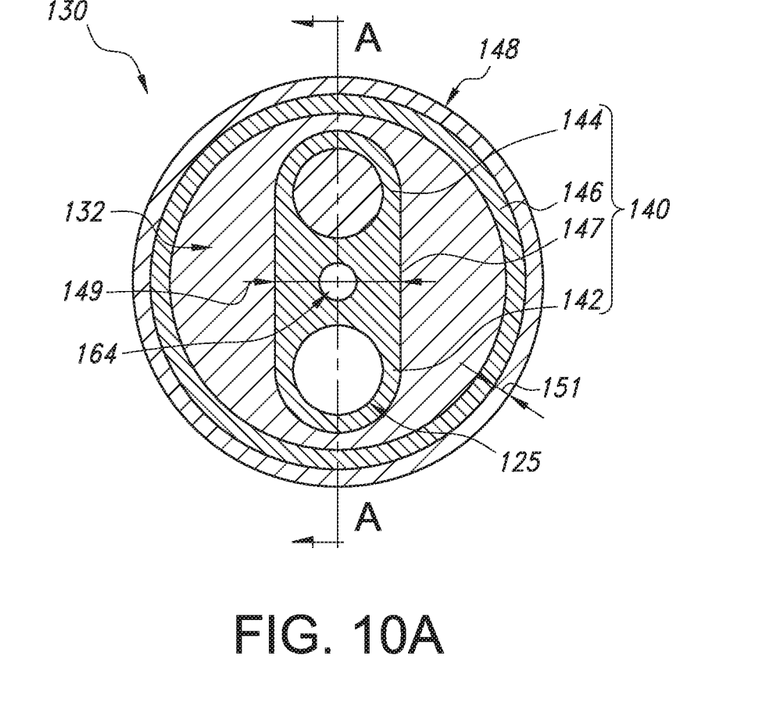
FIG. 10A depicts another embodiment of a rotatable adapter of the rotatable assembly of FIGS. 3A and 3B that includes an opening for receiving a snap-ring feature for coupling the rotatable assembly with the manifold.
Figure 10B:
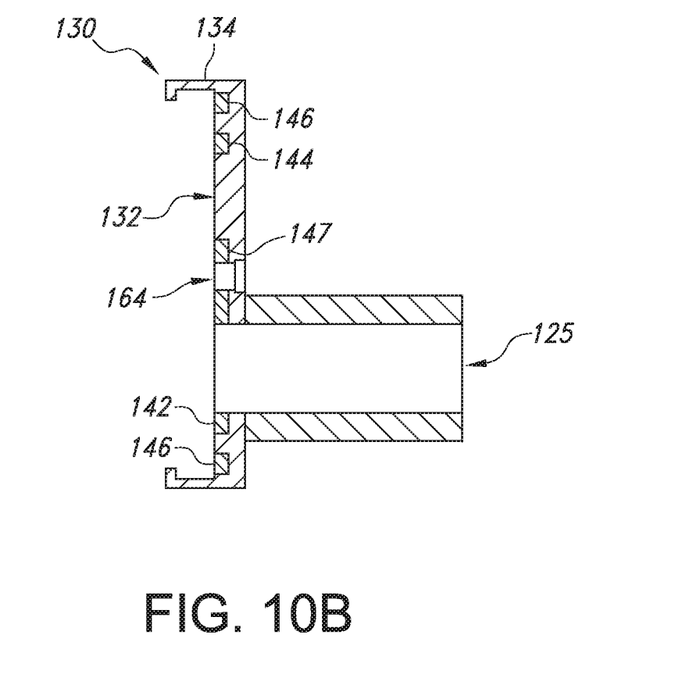
FIG. 10B is a section view of the rotatable adapter of FIG. 10A along section A-A of FIG. 10A.
Figure 10C:
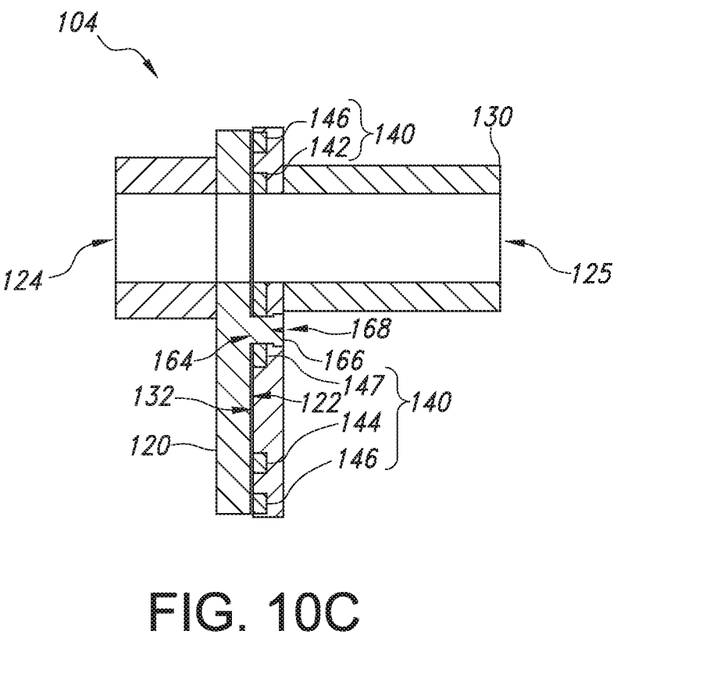
FIG. 10C depicts a cross-sectional side view of the rotatable assembly of FIGS. 10A and 10B coupled with a manifold including a snap-ring feature that is received within the opening of the rotatable assembly.

FIGS. 10A and 10B illustrate another embodiment of the rotatable adapter 130. The rotatable adapter 130 may include an opening 164, for example at a center of the rotatable adapter 130. Referring to FIG. 10C, the manifold 120 may include a snap-ring feature 166 that protrudes from the first mating surface 122 of the manifold. The snap-ring feature 166 may be configured to be received in the opening 164 of the rotatable adapter 130 to couple the rotatable adapter 130 with the manifold 120. The snap-ring feature 166 may include a slot 168 configured to collapse such that the snap-ring feature 166 can fit through the opening 164. In such embodiments, the rotatable assembly 104 may not include a snap-ring feature 134 as described above with reference to FIGS. 3A and 3B.

The material particularly shown and described above is not meant to be limiting, but instead serves to show and teach various exemplary implementations of the present subject matter. As set forth in the attached claims, the scope of the present invention includes both combinations and sub-combinations of various features discussed herein, along with such variations and modifications as would occur to a person of skill in the art.

What is claimed is:

1. A respiratory access assembly comprising:
a manifold having a first mating surface defining a single port opening, said single port opening being a first port opening;
a rotatable adapter having a second mating surface defining a single port opening, said single port opening being a second port opening; and
a seal assembly disposed between the manifold and the rotatable adapter, the seal assembly comprising a first seal ring, a second seal ring, an outer seal ring disposed proximate an outer perimeter of at least one of the manifold or the rotatable adapter, and a connection portion connected between the first seal ring and the second seal ring;

wherein the rotatable adapter is rotatable relative to the manifold between a single port open and closed configuration, wherein the connection/disconnection between the first port opening and the second port opening forms the single port open and closed configuration, wherein in the open configuration the first port opening of the manifold is aligned with the second port opening and sealed with the second port opening by the first seal ring of the seal assembly to form a fluid connection between the first port opening of the manifold and the second port opening of the rotatable adapter, and wherein in the closed configuration the first port opening of the manifold is sealed with a portion of the second mating surface of the rotatable adapter and the second seal ring of the seal assembly, wherein the connection portion forms a seal between the first mating surface and the second mating surface between the first seal ring and the second seal ring, and wherein the seal assembly is countersunk with respect to the first mating surface or the second mating surface of the manifold such that an outer sealing surface of the seal assembly is planar and the outer sealing surface of the seal assembly is flush with either the first mating surface or the second mating surface.

2. The respiratory access assembly of claim 1, wherein the seal assembly further comprises at least one spoke connected between the outer seal ring and at least one of the first seal ring and the second seal ring.

3. The respiratory access assembly of claim 1, wherein the seal assembly further comprises a continuous surface defined between the outer seal ring and each of the first seal ring and second seal ring.

4. The respiratory access assembly of claim 3, wherein the outer seal ring comprises a portion of the seal assembly proximate a perimeter of the seal assembly that is raised relative to the continuous surface in a direction perpendicular to the continuous surface.

5. The respiratory access assembly of claim 3, wherein at least one of the first seal ring and the second seal ring comprises a portion of the seal assembly that is raised relative to the continuous surface in a direction perpendicular to the continuous surface.

6. The respiratory access assembly of claim 1, wherein the seal assembly is attached to at least one of the manifold or rotatable adapter.

7. The respiratory access assembly of claim 6, wherein the seal assembly is over molded onto the first mating surface of the manifold or the second mating surface of the rotatable adapter.

8. The respiratory access assembly of claim 1, further comprising a ventilator manifold that is configured to be attached to an artificial airway that extends into a respiratory tract of a patient, and wherein at least one of the first port opening or second port opening is coupled with the ventilator manifold.

9. The respiratory access assembly of claim 1, further comprising a catheter assembly comprising a catheter tube, and wherein at least one of the first port opening or second port opening is coupled with the catheter assembly such that the catheter tube is slidable through the first port opening and second port opening when the rotatable adapter is in the open configuration.

10. The respiratory access assembly of claim 1, wherein one of the manifold or rotatable adapter comprises a snap ring feature that is configured to engage a portion of another of the manifold or rotatable adapter to couple the manifold and rotatable adapter together.

11. A method of forming a respiratory access assembly, the method comprising:
   forming a manifold having a first mating surface defining a single port opening, said single port opening being a first port opening;
   forming a rotatable adapter having a second mating surface defining a single port opening, said single port opening being a second port opening; and
   arranging a seal assembly between the first mating surface of the manifold and the second mating surface of the rotatable adapter, the seal assembly comprising a first seal ring, a second seal ring, an outer seal ring disposed proximate an outer perimeter of at least one of the manifold or the rotatable adapter, and a connection portion connected between the first seal ring and the second seal ring;
   wherein the rotatable adapter is rotatable relative to the manifold between a single port open and closed configuration, wherein the connection/disconnection between the first port opening and the second port opening forms the single port open and closed configuration,
   wherein in the open configuration the first port opening of the manifold is aligned with the second port opening and sealed with the second port opening by the first seal ring in the seal assembly to form a fluid connection between the first port opening of the manifold and the second port opening of the rotatable adapter, and wherein in the closed configuration the first port opening of the manifold is sealed with a portion of the second mating surface of the rotatable adapter and the second seal ring of the seal assembly,
   wherein the connection portion forms a seal between the first mating surface and the second mating surface between the first seal ring and the second seal ring, and
   wherein the seal assembly is countersunk with respect to the first mating surface or the second mating surface of the manifold such that an outer sealing surface of the seal assembly is planar and the outer sealing surface of the seal assembly is flush with either the first mating surface or the second mating surface.

12. The method of claim 11, wherein at least one of forming the manifold or forming the rotatable adapter comprises injection molding at least one of the manifold and the rotatable adapter.

13. The method of claim 11, wherein arranging the seal assembly between the first mating surface of the manifold and the second mating surface of the rotatable adapter comprises attaching the seal assembly to at least one of the first mating surface of the manifold and the second mating surface of the rotatable adapter.

14. The method of claim 11, wherein arranging the seal assembly between the first mating surface of the manifold and the second mating surface of the rotatable adapter comprises over molding the seal assembly to at least one of the first mating surface of the manifold and the second mating surface of the rotatable adapter.

15. The method of claim 11, further comprising integrally forming a snap ring feature with one of the manifold or the rotatable adapter that is configured to engage a portion of another of the manifold or rotatable adapter to couple the manifold and rotatable adapter together.

* * * * *